US012808865B2

(12) United States Patent
Hentz et al.

(10) Patent No.: US 12,808,865 B2
(45) Date of Patent: Nov. 24, 2026

(54) SENSOR FOR DETECTING A TARGET ANALYTE IN A LIQUID MEDIUM WITH AN OPTICAL RESONATOR COUPLED TO A MECHANICAL RESONATOR

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE PARIS CITE, Paris (FR)

(72) Inventors: Sebastien Hentz, Grenoble Cedex (FR); Thomas Alava, Grenoble Cedex (FR); Ivan Favero, Paris (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE PARIS CITE, Paris (FR)

( * ) Notice: Subject to any disclaimer, the term of this patent is extended or adjusted under 35 U.S.C. 154(b) by 1124 days.

(21) Appl. No.: 17/791,182

(22) PCT Filed: Jan. 8, 2021

(86) PCT No.: PCT/FR2021/050022

§ 371 (c)(1),
(2) Date: Jul. 6, 2022

(87) PCT Pub. No.: WO2021/140302

PCT Pub. Date: Jul. 15, 2021

(65) Prior Publication Data

US 2023/0081434 A1 Mar. 16, 2023

(30) Foreign Application Priority Data

Jan. 8, 2020 (FR) ....................................... 2000129

(51) Int. Cl.
*B01L 3/00* (2006.01)
*G01N 33/543* (2006.01)

(52) U.S. Cl.
CPC .............................. *G01N 33/54373* (2013.01)

(58) Field of Classification Search
None
See application file for complete search history.

(56) References Cited

U.S. PATENT DOCUMENTS

2013/0295688 A1 11/2013 Bailey et al.
2015/0024507 A1 1/2015 Han et al.
2019/0003975 A1 1/2019 Bailey et al.
2021/0096152 A1* 4/2021 Dietrich ............... G01Q 10/045

FOREIGN PATENT DOCUMENTS

WO WO 2012/061778 A2 5/2012
WO WO 2013/169393 11/2013

OTHER PUBLICATIONS

M. Hermouet et al. "1 million-Q optomechanical microdisk resonators for sensing with very large scale integration" *Microfluidics, Bio MEMS, and Medical Microsystems XVI*, Feb. 19, 2018, 5 pages.
King Yan Fong et al. Nano-Optomechanical Resonators in Microfluidics *Nano Letters*, US, vol. 15, No. 9, Aug. 4, 2015, pp. 6116-6120, 5 pages.
Matthew R. Foreman et al. "Whispering gallery mode sensors" *Advances in Optics and Photonics*, vol. 7, No. 2, May 22, 2015, pp. 168-240, 73 pages.
Martin Baaske et al. "Optical Resonator Biosensors: Molecular Diagnostic and Nanoparticle Detection on an Integrated Platform" *CHEMPHYSCHEM*, vol. 13, No. 2, Feb. 1, 2012, pp. 427-436, 10 pages.
Stanley M. Lo et al. "Photonic crystal microring resonator for label-free biosensing" *Optics Express*, vol. 25, No. 6, Mar. 16, 2017, pp. 7046-7054, 9 pages.
Ya-Nan Zhang et al. "Optical bio-chemical sensors based on whispering gallery mode resonators" *Nanoscale*, Royal Society of Chemistry, United Kingdom, vol. 10, No. 29, Jan. 1, 2018, pp. 13832-13856, 25 pages.
Miqin Zhang et al., "Proteins and cells on PEG immobilized silicon surfaces" *Biomaterials*, vol. 19, Jan. 10, 1998, pp. 953-960, 8 pages.
Thomas Demes et al., "DNA grafting on silicon nanonets using an eco-friendly functionalization process based on epoxy silane" *Materials Today: Proceedings* vol. 6, 2019, pp. 333-339, 7 pages.
Zhan-Hui Wang et al., "Silicon surface modification with a mixed silanes layer to immobilize proteins for biosensor with imaging ellipsometry", vol. 34, Dec. 16, 2003, pp. 173-177, 5 pages.
Yan Li et al., "Rapid Grafting of Azido-labeled Oligo(ethylene glycol)s onto an Alkynyl-terminated Monolayer on Non-oxidized Silicon via Microwave-assisted "Click" Reaction," *NIH Public Access, Author Manuscript, Langmuir*, vol. 27, No. 6, Mar. 15, 2011, pp. 1-23, 23 pages.

(Continued)

*Primary Examiner* — Christopher M Gross
(74) *Attorney, Agent, or Firm* — Oblon, McClelland, Maier & Neustadt, L.L.P.

(57) ABSTRACT

A concentration sensor for at least one biological species in the blood includes a support, at least one waveguide, and an optomechanical resonator suspended from the support. The optomechanical resonator is optically coupled to the waveguide, and the optomechanical resonator is configured to vibrate in volume mode and includes at least one face extending in the plane of the sensor and configured to receive molecules of the given species. At least the face includes a functionalisation layer specific to the species, the optomechanical resonator having a smaller dimension in a direction normal to the plane of the sensor compared with the dimensions of the said face.

20 Claims, 4 Drawing Sheets

(56) References Cited

OTHER PUBLICATIONS

Vincent T. K. Sauer, et al., "Single laser modulated drive and detection of a nano-optomechanical cantilever," *AIP Advances*, vol. 7, Jan. 30, 2017, pp. 015115-015115-7, 8 pages.
V T K Sauer, et al., "Optical racetrack resonator transduction of nanomechanical cantilevers", *Nanotechnology*, Jan. 2014, pp. 1-24, 25 pages.
José Juan-Colás et al., "The electrophotonic silicon biosensor", *Nature Communications*, Sep. 14, 2016, pp. 1-7, 7 pages.
E. Gil-Santos, et al., "High frequency nano-optomechanical disk resonators in liquids", pp. 1-21.
Thomas Braun et al., "Quantitative time-resolved measurement of membrane protein-ligand interactions using microcantilever array sensors", *nature nanotechnology*, vol. 4, Mar. 18, 2009, pp. 179-185, 7 pages.
L. Ding et al., "Wavelength-sized GaAs optomechanical resonators with gigahertz frequency", *Applied Physics Letters*, vol. 98, Mar. 15, 2011, pp. 113108-113108-3, 4 pages.
International Search Report mailed on Apr. 14, 2021 in PCT/FR2021/050022 filed on Jan. 8, 2021 (10 pages with English Translation).
Preliminary French Search Report dated Sep. 4, 2020 in French Application 2000129 filed on Jan. 8, 2020 (3 pages with English Translation of Categories of Cited Documents).
Written Opinion mailed on Apr. 14, 2021 in PCT/FR2021/050022 filed on Jan. 8, 2021 (7 pages).

* cited by examiner

SENSOR FOR DETECTING A TARGET ANALYTE IN A LIQUID MEDIUM WITH AN OPTICAL RESONATOR COUPLED TO A MECHANICAL RESONATOR

TECHNICAL FIELD AND PRIOR ART

The present invention relates to a concentration sensor for species in a liquid medium, in particular for biological species.

There are different techniques for detecting and quantifying biological species in a liquid. For example, the immuno-enzymatic ELISA ("Enzyme-linked immunosorbent assay") method, that is to say immuno-enzymatic assay on a solid support, is a laboratory test that detects the presence of an antibody or antigen in a sample.

This method implements an immunological test, wherein the assay is coupled to an enzyme-catalysed reaction that releases a coloured component followed by spectroscopy. This method is time-consuming and single-use.

There is also a method based on surface plasmon resonators. The attachment of a molecule to the surface is monitored by surface plasmon resonance, which detects changes in optical index at the surface, and allows the concentration of molecules to be deduced therefrom. This method is easy to use and fast, but it is not very sensitive.

There are also devices of the mechanical resonator type which include channels wherein a liquid containing the species to be detected circulates. The resonators operate under vacuum and have a high quality factor, however they are bulky and have low resolution. Furthermore, the functionalisation of the channels is complex due to the tortuosity and the dimensions of the channels. It is therefore difficult to produce specific sensors.

DESCRIPTION OF THE INVENTION

It is therefore a purpose of the present invention to provide a concentration sensor for species in a liquid medium offering good resolution and relatively simple and fast operation.

The purpose stated above is achieved by a sensor for the concentration of at least one species contained in a liquid including at least one optical resonator and at least one mechanical resonator coupled to each other, at least one guide wave optically coupled to the optical resonator, at least the mechanical resonator being at least partly functionalised so as to be selective with respect to said at least one species. The mechanical resonator vibrates in an in-plane volume mode of the sensor and at high frequency. Furthermore, the mechanical resonator has a small dimension in a direction normal to the plane of the sensor.

Thanks to the invention, the mechanical energy losses due to immersion in a liquid are significantly reduced, which allows to obtain a sensitive selective sensor.

Preferably, the mechanical resonator vibrates in radial mode.

In a preferred embodiment, the optical resonator and the mechanical resonator are formed by the same object.

Advantageously, the single resonator is carried by a foot of small diameter compared to the largest dimension of the surface of the resonator, for example the foot diameter/largest dimension ratio of the surface of the resonator <1/10.

Preferably, the functionalisation layer is thin, for example less than 20 nm thick, and is homogeneous, reducing optical losses. Furthermore, the implementation of a homogeneous layer simplifies the determination of the concentrations.

Preferably, the resonator is made of silicon, which allows easy large-scale manufacture.

The object of the present invention is therefore a concentration sensor structure for at least one given species in a liquid medium including a support, at least one waveguide, at least one optical resonator suspended from the support, said optical resonator being optically coupled to the waveguide, at least one mechanical resonator suspended from the support, said mechanical resonator and said optical resonator being coupled, said mechanical resonator being configured to vibrate in volume mode and including at least one face extending in the plane of the sensor and configured to receive molecules of said given species, at least said face including a functionalisation layer specific to said species, said mechanical resonator having a small dimension in a direction normal to the plane of the sensor compared with the dimensions of said face.

Preferably, the dimension of the mechanical resonator and/or of the optical resonator in the direction normal to the plane of the sensor is at least 10 times smaller than the dimensions of the mechanical resonator and/or of the optical resonator in the plane of the sensor.

The functionalisation layer is advantageously homogeneous. The functionalisation layer may have a thickness less than or equal to 20 nm.

Preferably, the mechanical resonator is configured to vibrate in a radial mode.

In an advantageous example, the mechanical resonator and/or the optical resonator is or are suspended by a foot connecting a face of the resonator(s) facing the support and the support. The foot may have a diameter at least 10 times smaller than the in-plane dimensions of the resonator(s).

In an exemplary embodiment, the optical resonator and the mechanical resonator are the same element suspended from the support, said element being an optomechanical resonator. The optomechanical resonator advantageously has the shape of a disc, a ring or a racecourse.

The concentration sensor structure may include means for exciting the mechanical resonator so as to vibrate it, preferably at its resonant frequency.

The concentration sensor structure may include several sets of coupled optical and mechanical resonators or several optomechanical resonators, coupled to a single waveguide.

The present invention also relates to a concentration sensor for at least one given species in a liquid medium including at least one sensor structure according to the invention, a light source connected to one end of the waveguide, and means for processing the light wave connected to the other end of the waveguide.

The light source is for example configured to emit multiplexed light waves and the processing means are configured to process the multiplexed light waves.

The present invention also relates to a measurement assembly including at least two sensors according to the invention, one of the sensors, called the first sensor, being functionalised with a first biological molecule specifically recognising the given species, the other sensor, called the second sensor, being functionalised with a second biological molecule similar in nature to the first molecule and having a capacity for specific recognition of a species other than the given species, said assembly including means for subtracting the signal emitted by the second sensor from the signal emitted by the first sensor.

The present invention also relates to a microfluidic system including at least one channel or the circulation of the liquid the concentration of at least one species of which is to be measured and at least one concentration sensor according to the invention or at least one assembly according to the invention, the optical resonator and the mechanical resonator or the optomechanical resonator being disposed in the channel.

The microfluidic system may include a channel with several sensors including functionalisation layers specific to species different from each other.

The channel has for example a height comprised between 5 μm and 500 μm and a width comprised between 10 μm and 700 μm.

BRIEF DESCRIPTION OF THE DRAWINGS

The present invention will be better understood on the basis of the following description and the appended drawings wherein.

DETAILED DESCRIPTION OF PARTICULAR EMBODIMENTS

Figure 1A:
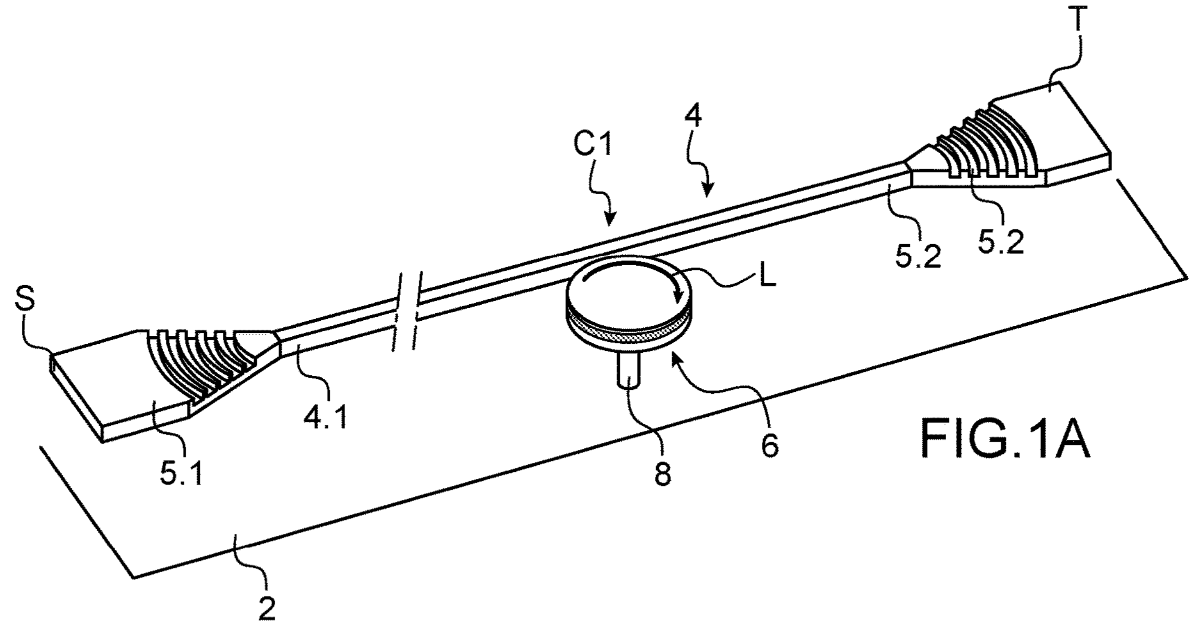
FIG. 1A is a perspective view of an example of a concentration sensor according to the invention.

FIG. 1A shows an example of concentration sensor C1 for species in a liquid medium according to the invention.

In the present application, the term "species" means biological species, such as bacteria or viruses, chemical molecules, atoms and/or nanoparticles.

As will be described below, the resonator is functionalised so as to have an affinity with the species to be detected. The functionalisation layer can be sensitive to biological species, to individual atoms or to nanoparticles. In the case of nanoparticles, the specificity can be directed against markers present on the surface of these nanoparticles or against the constituent atomic element of the nanoparticle. A specificity towards the size of the nanoparticles can also be considered.

The species to be detected have dimensions comprised between a few tens of nm to a few μm. Species have maximum dimensions less than or equal to the dimensions of the resonator in the plane, which will be described below.

The liquid can be blood, plasma, humours, and more generally any bodily liquid, water from watercourses, such as rivers, ocean water, water from networks of city water supply . . . and any other liquid that is to be analysed.

The sensor C1 includes a support or substrate 2, at least one waveguide 4 supported by the substrate and an optomechanical resonator 6 suspended from the substrate 2, a light source S and means T for processing the light wave leaving the waveguide. The support 2, the waveguide, the optomechanical resonator forms a sensor structure.

The waveguide 4 includes an input end 4.1 of a light wave connected to a light source via a coupling network 5.1, and an output end 4.2 connected to processing means of the light wave leaving the waveguide via a coupling network 5.2.

The resonator 6 is disposed close to a side of the waveguide 4 so as to be optically coupled thereto. The waveguide is in the evanescent field of the resonator, so that the light wave coming from the source is injected into the optical resonator and the light wave having circulated in the resonator is collected by the waveguide.

The width of the space between the side of the waveguide and the lateral edge of the resonator is for example comprised between 10 nm and 50 nm.

Figure 1B:
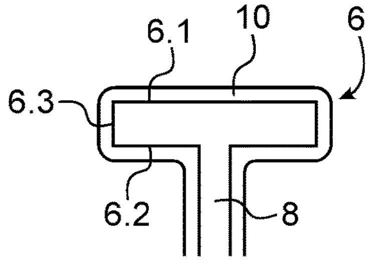
FIG. 1B is an enlarged view of the optomechanical resonator of FIG. 1A.

In the example shown, the optomechanical resonator 6 has the shape of a disc suspended from a foot 8 attached to a face of the disc facing the substrate. The disc extends in a plane of the sensor. The resonator includes two end faces 6.1, 6.2 substantially parallel to the plane of the sensor and a lateral face 6.3 (FIG. 1B).

In the present application, the term "plane of the sensor" means a plane parallel to the substrate.

Preferably the foot has a small diameter compared to the dimensions of the disc in the plane of the sensor, more particularly a small diameter compared to the diameter of the disc, preferably the foot has a diameter 10 times smaller than the diameter of the disc.

More generally, the diameter of the foot is ten times smaller than the smallest dimension of the resonator in the plane of the sensor, thus the foot interferes little or not with the radiation vibration of the resonator.

In a variant, the resonator is suspended by in-plane springs or by radially extending nano-sized beams compressed and tensioned by the vibration of the disc. The springs or the beams are then sized to have a lower axial stiffness than that of the resonator.

Any other shape of resonator may be suitable, for example seen from above the resonator may have the shape of a ring, ellipse or racetrack.

The resonator can be made of any material capable of confining an electromagnetic wave, such as GaAS, Ge or Si. The latter is particularly interesting for a manufacture using microelectronic techniques offering a high level of integration on a substrate.

The resonator is intended to capture the species to be detected, the surface of the resonator is therefore preferably as large as possible to maximise the amount of species that can be captured.

However, it is sought to minimise the lateral surface 6.3 of the resonator in order to limit the viscous losses by interaction with the solvent and to promote shearing. It is therefore sought to maximise the end surfaces 6.1, 6.2 of the resonator and to reduce the side surface 6.3. It is also sought to reduce the mass of the optomechanical resonator in order to have good mass sensitivity.

The shape of the disc is therefore particularly advantageous in terms of surface ratio. Preferably, a resonator having a large aspect ratio, a large in-plane dimension of the sensor/thickness of the resonator ratio is selected.

In the case of a disc, the diameter of the disc/thickness ratio is preferably comprised between 10 and 100. The maximum diameter of the resonator is preferably a few hundred μm.

In an exemplary embodiment, the resonator includes tapered edges advantageously improving the optical performance of the resonator.

The resonator is also such that it vibrates in an in-plane volume mode, allowing to reach a high vibration frequency, for example at least equal to 100 MHz.

Preferably, the resonator vibrates in a radial mode or RBM (Radial Breathing Mode), such a mode allows to achieve a very good coupling between the optical mode and the mechanical mode. Indeed, the radial vibration of the disc has a significant impact on the optical properties of the disc, in particular on the length of the optical path within the resonator and therefore on the light power recovered by the waveguide 2.

In a variant, the resonator can vibrate in a tangential mode or a wine glass mode. Nevertheless, it has a reduced efficiency compared to the resonator in a radial mode.

The resonator is further functionalised so as to be specific to one or more species to be detected. The functionalisation is obtained by forming a layer 10 (FIG. 1B) specific to the species to be detected on all the surfaces of the resonator 6.1, 6.2, 6.3 or part of the surfaces of the resonator.

For example, the functionalisation layer includes at least one macromolecule capable of specific recognition of a target, i.e. the given species to be detected.

The functionalisation of the multi-species resonator is obtained for example by functionalising different parts of the resonator, each specific to one species, or by producing a functionalisation layer which mixes different bioreceptors each specific to one species.

By way of example, the functionalisation layer includes antibodies specific to a protein or to a small molecule, for example a toxin, aptamers specifically recognising a protein or a small molecule, DNA or RNA strands which will hybridise with a strand of DNA or RNA complementary to that grafted onto the surface of the resonator, Molecular Imprinting Polymers (MIP).

The functionalisation of the surface of the resonator consists in modifying the molecules present on the surface of the sensor and/or in grafting onto the surface of the sensor the new molecules allowing the specific recognition of the target sought.

The modification of the molecules present on the surface of the sensor can for example consist, in a non-limiting manner, in the oxidation of a function, in the dehydration of an alcohol function, in the nucleophilic substitution of a group by another or in an esterification. All these transformations are well known to the person skilled in the art who will know how to go from one chemical function to that of interest.

Functionalisation by grafting may generally require an intermediate layer supporting the layer of new molecules providing the desired functionalisation. There are several methods for functionalising a silicon surface. A first method consists in grafting a layer of PEG (polyethylene glycol polymer chain) onto the silicon surface. One end of the PEG chain binds covalently to the silicon surface and the other end remains free, thus allowing the molecule of interest to be grafted for a specific recognition of the sensor. This method is described in document [1]. Another method consists in using carbon chains, one end of which has a silane function and the other end is selected so as to subsequently graft the molecule allowing the specific recognition of the sensor. The other end can be an epoxy function, subsequently allowing the grafting of DNA, or an amine function allowing the grafting of a protein, for example an immunoglobulin. This method is described in documents [2] and [3]. Finally, another method consists in grafting onto the silicon surface an alkynene having an alkene function at one end and an alkyne function protected by a trimethylgermanyle group at the other end. After grafting onto the silicon surface, the alkyne function is used to couple the molecule of interest by click chemistry. This method is illustrated in document [4].

The functionalisation layer 8 has a small thickness, or even includes a single layer of functionalisation molecules. Advantageously, the thickness of the functionalisation layer is less than 20 nm, and preferably less than 10 nm. Furthermore, the layer has a constant thickness over the entire surface.

In the present application, the term "constant thickness" means a layer whose thickness varies at most by 25% of its thickness over its entire surface.

Furthermore, the functionalisation layer is very advantageously homogeneous on the surface of the resonator, i.e. it includes a relatively uniform number of molecules per surface unit.

The homogeneity of the layer corresponds to the amount of target recognition sites to be detected per surface unit, which is a multiple of the number of immobilised bioreceptor molecules per surface unit on the surface of the resonator. A surface unit is defined as being at least $1/100^{th}$ of the sensor area. A layer is called homogeneous layer when the number of grafting/recognition sites available in each surface unit varies by less than $5/100^{th}$ around an average value. The number of recognition sites per surface unit depends on the functionalisation protocol selected and the size of the bioreceptor molecule.

The implementation of a fine and advantageously homogeneous functionalisation layer allows to preserve the optical coupling and optomechanical coupling properties of the resonator after functionalisation.

Furthermore, the implementation of a homogeneous layer makes it relatively easy to trace the concentration of the species.

In addition, the implementation of a homogeneous functionalisation layer improves the sensitivity of the sensor and allows to put a functionalisation layer without degrading the measurements of the sensor.

In addition, in the case where the functionalisation layer covers the lateral edge of the resonator and possibly the sides of the waveguide, and therefore intervenes in the optical coupling between the waveguide and the resonator, the production of a thin and homogeneous layer reduces optical losses.

The implementation of a thin layer limits the risks of filling the space between the waveguide and the resonator. For example, for a wavelength of 1.55 μm, the width of the optical coupling space is comprised between 20 nm and 500 nm. It is therefore possible to choose a thickness of the layer that is sufficiently thin, so that, when it covers both the side of the waveguide and the lateral edge of the resonator, the space is not filled.

The functionalisation layer can be localised, advantageously it can be deposited only on the end faces of the resonator, or even on only one of the end faces. In this case, the functionalisation layer does not intervene in the optical coupling between the waveguide and the resonator.

The operation of the sensor will now be described.

The wavelength of the light wave to be injected into the resonator will be selected close to the optical resonance of the resonator, i.e. at the side of the optical resonance peak. The light resonating inside the optical resonator is then very sensitive to the mechanical deformation of the mechanical resonator, in particular when the optical and mechanical resonator are coincident)

The light wave at the selected wavelength is injected into the waveguide by a light source, the light wave is injected by optical coupling into the optomechanical resonator 6. L denotes the light wave circulating in the resonator. The modulation frequency of the power of the light wave is selected so as to vibrate the resonator in a volume mode, advantageously in a radial mode.

The sensor is immersed in a liquid, the concentration of a given species of which is to be measured and for which the sensor has an adapted functionalisation layer. The molecules of the given species are then captured by the functionalisation layer and attach themselves to the resonator, which modifies the mass of the resonator and therefore the vibration frequency of the resonator. The measurement of the variation of the vibration frequency allows to determine the amount of given species deposited on the resonator and to determine the concentration.

In a variant, the measurement of the variation in the vibration frequency can be combined with a measurement of the variations in the optical properties of the resonator, allowing to acquire additional information.

Preferably, before the circulation of the sample containing the target to be detected, a biological buffer solution having a viscosity similar to that of the sample containing the target circulates around the sensor which allows the sensor to reach a stable resonant frequency. Then, the sample containing the target is injected and the sensor perceives the change in resonance frequency coming from the grafting of the target on the resonator. This response of the sensor to the biological grafting has a dynamic in $N^*e^{-x/t}(k=Ae^{(Ea/RT)})$ and lasts of the order of 5 min to 40 min in practice.

In an advantageous example, several sensors are used.

In a two-sensor configuration, the first sensor is functionalised with a first biological molecule that specifically recognises the target. The second sensor is functionalised with a second biological molecule similar in nature to the first molecule, but having a specific recognition capacity of a species other than the desired target.

The signal emitted by the first sensor contains information on the specific attachment of the target and information on the non-specific attachment, of elements other than the one sought, which is parasitic information. The signal emitted by the second sensor only contains information on the non-specific attachment. By subtracting the signal of the second sensor from the signal of the first sensor, information is obtained on the specific grafting, which allows to detect the presence of the target sought.

After a measurement taken by the sensor, it can be cleaned.

According to an example of rinsing, a biological buffer solution is sent to the sensor through the fluid supply system. This solution causes the detachment of part of the targets immobilised on the sensor. Some targets may remain on the surface of the sensor, immobilised on their corresponding bioreceptors. These remaining elements cause a decrease in the amount of sites available for subsequent analyses with the same sensors.

Nevertheless, the sensor according to the invention has great sensitivity and is therefore particularly adapted for detecting only a very small number of target molecules. The detection can often be done with the recognition of a number of target elements representing only a portion of the graftable targets entirely on the surface of the sensor. Thus, the sensors can, in particular in the application for detecting a small number of target molecules, carry out several successive analyses, because the samples analysed do not contain enough target elements to saturate the surface of the sensor.

When it is desired to force the separation of the remaining target elements in order to release all the bioreceptors. Several techniques can be used to be adapted according to the target molecules.

In the case of hybridised DNA strands (target and bioreceptor), the temperature of the sensor can be increased to 80° C. for a period of a few minutes, for example by means of an attached heating device, which causes the dehybridisation of any DNA-DNA complex and releases the targeted elements from the surface of the disc. A biological buffer-type rinsing solution can circulate simultaneously to collect the released elements.

For recognition of proteins-proteins or proteins-other biological element to be detected, such as toxins, bacteria, cells, weakly concentrated solutions of NaOH soda or guanadinium hydrochloride can be used which can cause the dissociation of the antigen-antibody binding and completely regenerate the sensor before further measurements. Regeneration can nevertheless degrade the receptor proteins, limiting the number of possible regenerations, for example depending on the functionalised surface, the number of regenerations can be comprised between 10 and 40.

In the operating example described above, the resonator is vibrated by the measurement light wave.

In a variant, the resonator is not vibrated by the light wave. Only the resonance frequency variation is measured thanks to the Brownian noise of the resonator, indeed the thermal agitation causes the resonator to vibrate at its resonant frequency. In this variant, the light wave is only used to detect the variation in vibration frequency.

Figure 2:
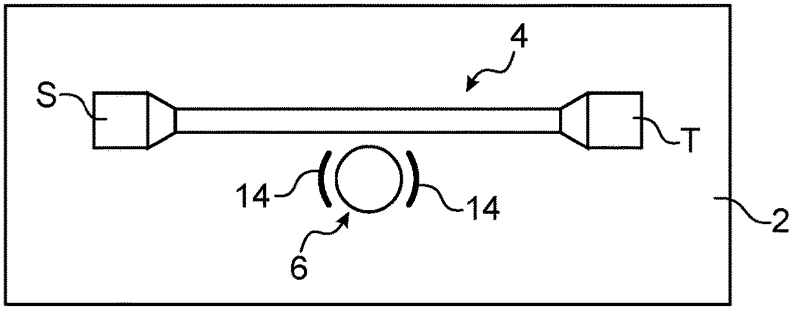
FIG. 2 is a schematically represented top view of an example of a concentration sensor including excitation means.

In an advantageous variant, the sensor shown in FIG. 2 includes specific excitation means 14 for vibrating the resonator, at its resonant frequency, which allows great sensitivity in the reading of mechanical frequency changes, and preferably at a large amplitude to maximise the signal to noise ratio. The vibration of the resonator improves the resolution.

The grafting of biological targets increases the mass of the mechanical resonator, which modifies its resonance frequency, which is transduced by the optical resonator forming a transducer.

Therefore, optical means for optically resonating the optical resonator and means for mechanically resonating the mechanical resonator can coexist. The optical resonator forms a transducer, which then transduces the mechanical resonance into light then electrical information.

In an advantageous embodiment, the optical resonator which is the means for transducing the mechanical resonance can also be the mechanical resonance means, for example by modulating the light power injected into the optical circuit by a modulator.

In this example the excitation means 14 are of the electrostatic type, they include a first electrode 14.1 formed on the lateral edge of the resonator 4 for example by doping the silicon and a second electrode 14.2 formed on the support facing the first electrode.

In a variant, the excitation means are of the optical by radiation pressure type, for example using a mode called "pump-probe" mode using a light signal of wavelength different from the light signal used for the measurement, and whose amplitude is modulated at the resonant frequency of the disc. In a variant, use is made of a single light signal which provides both measurement and excitation; said light signal is modulated by means of an electro-optical modulator.

In an advantageous variant, a phase lock loop is integrated which allows to servo-control the phase of the vibration to the resonance.

Advantageously, a resonator of reduced mass is produced in order to increase the sensitivity of the sensor.

Figure 3:
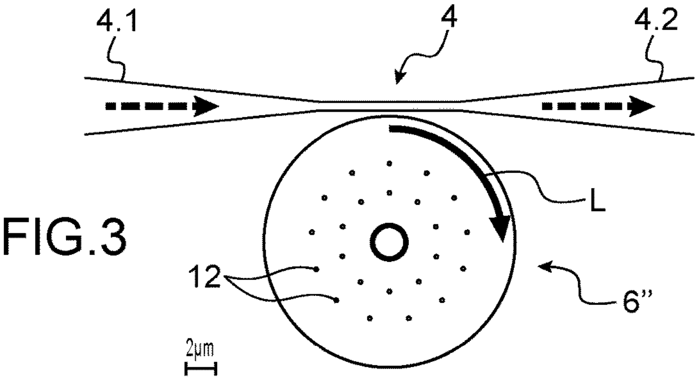
FIG. 3 is a schematically represented top view of a concentration sensor whose resonator including holes allowing to increase its accuracy.

This can be obtained by making through holes 12 in the resonator 6", as shown in FIG. 3. The holes 12 offer the additional advantage of increasing the specific surface covered by functionalisation layer. The holes are for example in the direction normal to the plane of the resonator. Furthermore, these holes can advantageously be used to facilitate the release of the resonator, when it is released by etching the sacrificial layer in a microelectronic method.

When the foot is made of the material of the sacrificial layer, for example $SiO_2$, its diameter before release is selected so that at the end of the etching the "remaining" diameter is sufficient to support the resonator.

Figure 4:
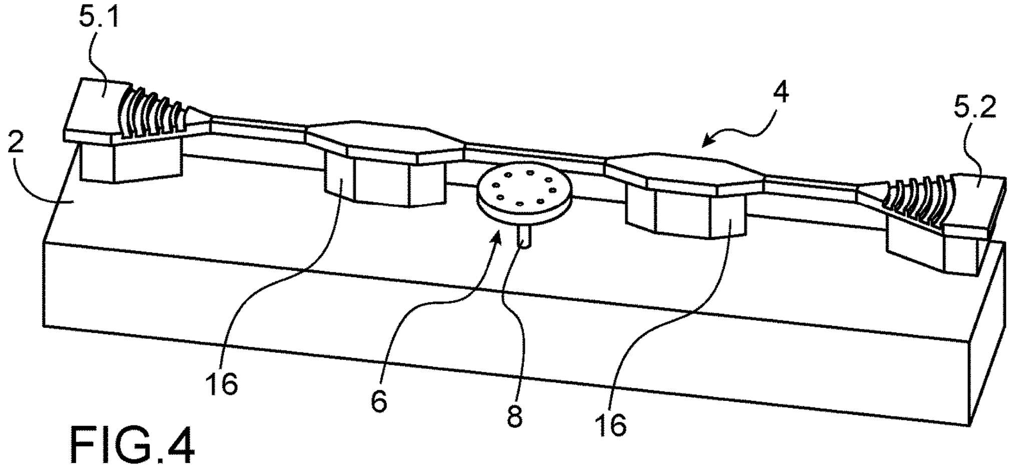
FIG. 4 is a perspective view of another example of a concentration sensor with a particular waveguide structure.

FIG. 4 shows an exemplary embodiment of an advantageous sensor when the waveguide is supported by portions of the sacrificial layer.

During the release of the resonator, it is not desired to completely release the waveguide 2, nor the coupling networks.

Moreover, the width of the waveguides is determined to obtain particular optical properties (for example, to be optically single mode). When this width is small compared to the distances to be etched under the resonator, wider waveguide portions 16 are advantageously provided at a distance from the areas of coupling with the resonator and/or close to the connections between the waveguide and the coupling networks 5.1, 5.2.

Thus the sacrificial layer under the portions 16 are not entirely etched and serve as a support for the waveguide. The width of the portions 16 is selected so as to be at least equal to the maximum distance to be etched in the plane+a width sufficient to support the waveguide.

In the example shown the portions 16 are regularly distributed along the waveguide but this is not limiting.

Figure 5:
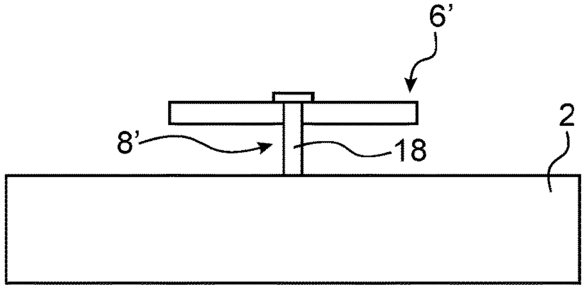
FIG. 5 is a side view of an embodiment of a resonator that can be implemented in the concentration sensor according to the invention.
Figure 6:
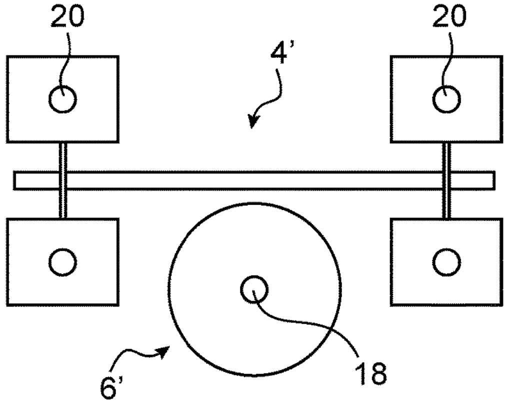
FIG. 6 is a top view of an example of a sensor implementing the resonator of FIG. 5.

In another advantageous exemplary embodiment shown in FIGS. 5 and 6, allowing to overcome the etching problems, the foot 8' of the resonator 6' and/or the supports of the waveguide 4' are made by vias 18, 20 made of a material insensitive to etching upon release. For example, when release is obtained by etching silicon oxide with HF, the vias are made of polysilicon or metal.

The waveguide is coupled to the light source and to the analysis device, for example by optical fibres positioned at an optimal angle thanks to piezoelectric positioners above the coupling networks. Advantageously, it is possible to use a fibre-drawing technique consisting of "gluing" fibres directly onto the chip.

Figure 7:
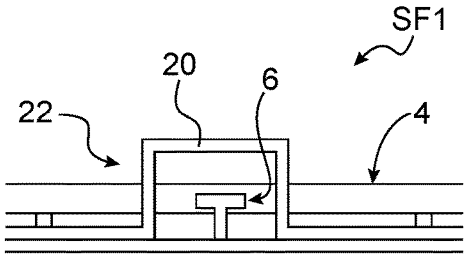
FIG. 7 is a schematic representation of an example of a microfluidic system implementing at least one concentration sensor according to the invention.

FIG. 7 shows an example of a microfluidic system integrating the sensor.

The system SF1 includes a microchannel 20 for example formed in a cover 22 which is attached to the substrate. The liquid to be analysed is injected into the channel 20. The dimensions of the channel are such that the liquid is forced to circulate at the resonator only. Thus, this maximises the probability of capturing the species to be detected and reduces the analysis time. Furthermore, the volume of liquid required can be reduced. A typical microchannel can measure from 5 μm to 500 μm in height and from 10 μm to 700 μm in width.

In the example shown, the system includes a single sensor and the waveguide is transverse to the channel.

In a variant, the system includes several sensors disposed one after the other and functionalised differently and each coupled to its own waveguide. Thus with a single system it is possible to determine the concentrations of several species in the same sample of liquid and almost simultaneously.

In a variant, the waveguide is aligned with at least part of the channel and several resonators are coupled thereto and by multiplexing it is possible to carry out the detection of several species, or even to carry out positive controls, for example by using two sensors, a first sensor functionalised with a bioreceptor molecule and having specificity towards the molecule sought and a second sensor functionalised with a bioreceptor molecule of the same type as the first sensor, but not having specificity towards the molecule sought.

Figure 8:
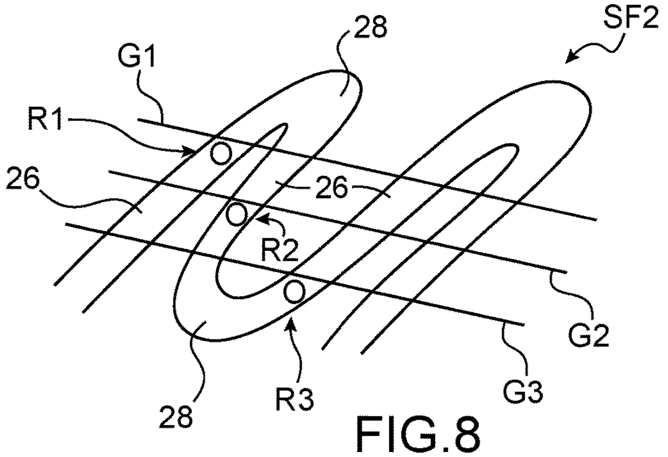
FIG. 8 is a schematic representation of another example of a microfluidic system implementing at least one concentration sensor according to the invention.

FIG. 8 shows another example of a microfluidic circuit SF2 including a serpentine-shaped channel 24 comprising straight portions 26 connected by curved portions 28 and a resonator R1, R2, R3 located in a straight portion 26 and waveguides G1, G2, G3 coupled to each resonator, and transverse to the straight portions.

In a variant, the resonators are coupled to the same waveguide and the detection is performed by multiplexing.

Figure 9:
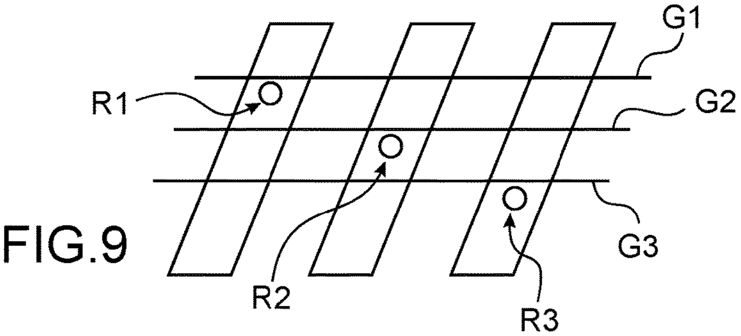
FIG. 9 is a schematic representation of another example of a microfluidic system implementing at least one concentration sensor according to the invention.

FIG. 9 shows yet another example of a microfluidic system SF3 which differs from the system of FIG. 8 in that the straight portions 26 are not connected by curved portions and form independent microchannels which can be supplied by different liquids.

Advantageously, the functionalisation can be carried out by circulating the functionalisation liquid in the channel during manufacture.

In the case of the system SF2, it is advantageous to make beforehand only the straight portions which are functionalised with different liquids, thus each resonator has its own functionalisation and then the curved portions are made so as to form a single system with resonators having different functionalities.

Figure 10:
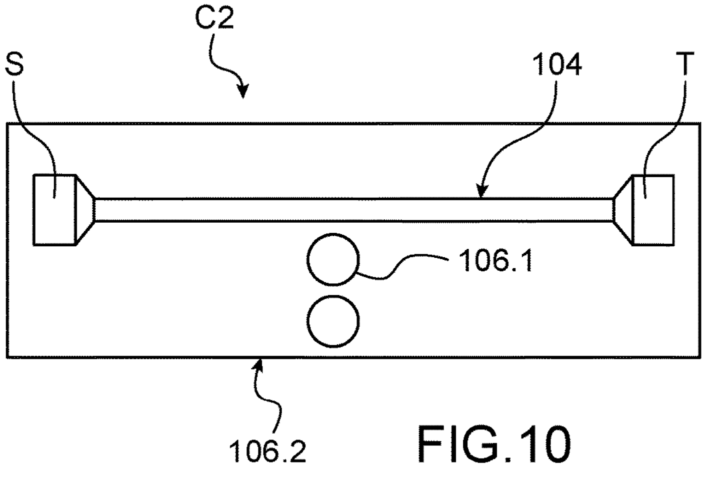
FIG. 10 is a schematic representation of an example of a sensor including an optical resonator and an optical resonator that are separate and coupled to each other.

FIG. 10 shows an example of a sensor wherein the optical resonator and the mechanical resonator are separate.

The sensor C2 includes a sensor structure comprising a substrate 102, a waveguide 104, an optical resonator 106.1 optically coupled to the waveguide 104 and a mechanical resonator 106.2 disposed in the evanescent field of the optical resonator 106.1 and capable, due to its mass modification by capture of the particles, to modify the optical properties of the optical resonator. The sensor C2 also includes a light source S connected to one end of the waveguide 104 and processing means T connected to the other end of the waveguide 104.

The mechanical resonator 106.2 vibrates in volume mode preferably in radial mode.

In this example, the mechanical resonator can have a discontinuous or irregular shape, for example a square shape since it is not intended to guide the light wave.

Preferably, the foot of the optical resonator and the foot of the mechanical resonator have a small diameter compared to the dimensions of the resonator in the plane of the sensor. In the case of disc-shaped resonators, the foot has a small diameter compared to the diameter of the disc, preferably the foot has a diameter 10 times smaller than the diameter of the disc.

More generally, the diameter of the foot is ten times smaller than the smallest dimension of the resonator in the plane of the sensor, thus the foot interferes little or not with the radiation vibration of the resonator.

Optical and mechanical resonators with a large aspect ratio, a large in-plane dimension of the sensor/thickness of the resonator ratio are preferably selected.

In the case of a disc, the Diameter of the disc/thickness ratio is preferably comprised between 10 and 100. The maximum diameter of the resonators is preferably a few hundred μm The mechanical resonator can be excited by external electrical means or by thermal agitation, in the latter case the signal-to-noise ratio is poorer.

Figure 12:
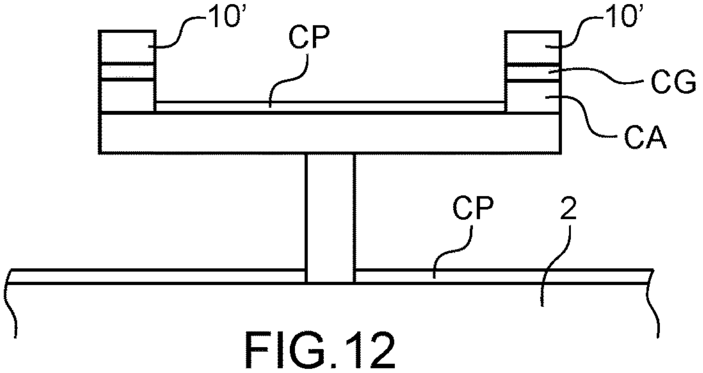
FIG. 12 is a schematic representation of another example of an optomechanical resonator according to the present invention.

FIG. 12 shows another example of a sensor according to the present invention wherein the functionalisation layer 10' is advantageously located on the peripheral edge of the resonator which allows to maximise the signal. The functionalisation layer has a ring shape and is located on the area of greatest displacement amplitude of the sensitive area of the resonator. By promoting the attachment of the particles of interest in this area, the signal is maximised. For example, the width of the functionalisation ring is at most equal to ⅓ of the radius of the resonator disc.

The functionalisation layer can be produced according to the methods described above. For example, a bonding layer CA, for example made of gold, in the shape of a ring is formed on the sensitive surface, on which is formed a grafting layer CG including, for example, a thiol function, and on which is produced the functionalisation layer formed for example by bioreceptors specific to the target particles, for example the bioreceptors are aptamers, antibodies, lectins, DNA or RNA strands, enzymes, . . .

Even more advantageously, the sensor includes a passivation layer CP blocking the absorption of the particles of interest, this layer is formed on the areas of the sensor where it is not desired to attach the target particles, i.e. on the areas other than those where the functionalisation layer is formed. The passivation layer CP is formed on the substrate and in the example shown on the central part of the sensitive surface inside the ring-shaped functionalisation layer 10'. Thus the attachment of the targets sought outside the sensitive area of the sensor is limited. The effective detection of lower concentrations of species within the liquid medium is then improved.

In the case where the functionalisation layer covers the entire sensitive surface of the sensor, the passivation layer is formed only on the substrate.

The passivation layer contains, for example, silanes of formula $X_3Si—(CH_2)nCH_3$. The part $X_3Si—$ allows the attachment to the silicon and the saturated aliphatic chain $—(CH_2)nCH_3$ prevents the grafting of the molecules of interest.

For example, X can be a halogen (Cl, Br . . . ) or an $R_3O—$ group ($R═CH_3—$, $CH_3CH_2—$ . . . ).

In another example, the passivation layer is a PLL-g-PEG (poly(L-lysine)-graft-poly(ethylene glycol) polymer. The Lysine part allows grafting on the substrate while the ethylene glycol chain, prevents the molecules from being grafted onto the substrate:

An example of a method for producing the sensor C1 will now be described on the basis of FIGS. 11A to 11D.

Figure 11A:
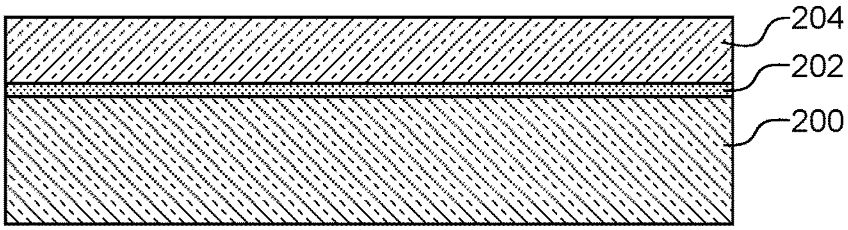
FIGS. 11A, 11B, 11C and 11D are schematic representations of elements obtained during steps of an example of a method for manufacturing a sensor according to the invention.

For example, an SOI (Silicon on Insulate) substrate is used including a polysilicon substrate 200, a layer of $SiO_2$ 202, for example 0.5 μm thick, and a monocrystalline silicon layer 204, for example 0.22 μm thick, shown in FIG. 11A.

During a first step, the structure of the sensor, i.e. the waveguide, the resonator(s) is defined by lithography, then etching. For example, the etching is Deep Reactive-Ion Etching or DRIE with a stop on the layer 202.

Figure 11B:
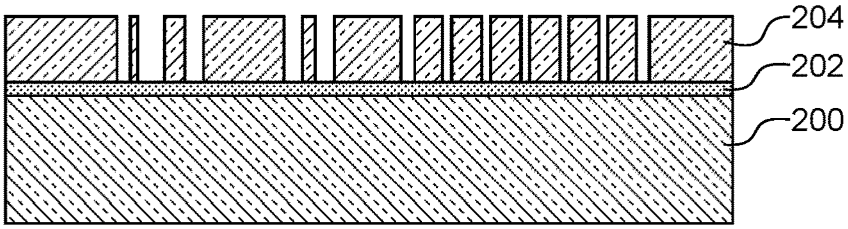

The element thus obtained is shown in FIG. 11B.

In the case of an electrostatically actuated sensor, during a next step, doping is carried out by localised implantation in order to produce conductive tracks.

Then a succession of depositions of layers of different metals is formed to form the electrical contacts. The stack of layers thus formed is for example Ti/TiN/Au. The layer is formed for example by deposition then the contacts 206 are defined by lithography then etching.

Figure 11C:
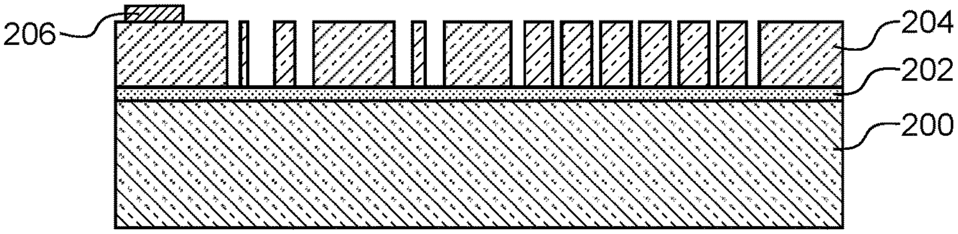

The element thus obtained is shown in FIG. 11C.

During a subsequent step, the structure, i.e. the resonator and the waveguide, is freed by at least partially etching the layer 202. The etching is carried out for example by wet etching or in the vapour phase with hydrofluoric acid. This is a time stamp.

Figure 11D:
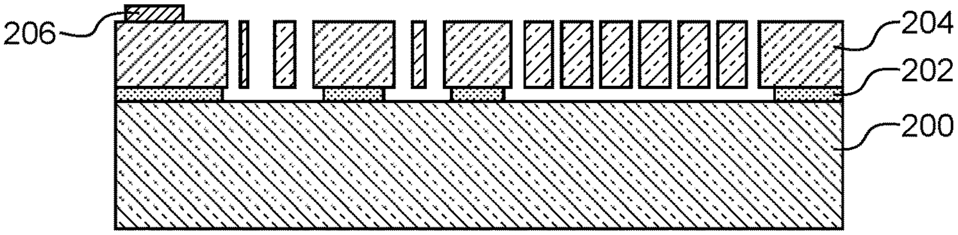

The element thus obtained is shown in FIG. 11D.

In the case of the sensor of FIG. 5, additional steps of forming the metal suspension rods are required, for example steps of producing metal vias well known to the person skilled in the art are carried out.

A functionalisation of the sensor is then carried out. It can be a functionalisation of the entire structure, the functionalisation layer being formed both on the resonator and on the waveguide, or else a localised functionalisation, i.e. for example only on the end faces of the resonator. The functionalisation layer can be produced using one of the techniques described above.

In the case of manufacturing a microfluidic system, the method further includes manufacturing a cover provided with at least one channel and sealed assembly of the cover and the sensor.

The functionalisation can then take place by circulation of a fluid ensuring the functionalisation of the resonator.

The sensor is advantageously made of silicon, which makes it particularly adapted for a high level of integration on a substrate.

REFERENCES

[1] Zhang, M., Desai, T. & Ferrari, M. Proteins and cells on PEG immobilised silicon surfaces. *Biomaterials* 19, 953-960 (1998).

[2] Demes, T. and al. DNA grafting on silicon nanonets using eco-friendly functionalisation process based on epoxy silane. *Materials Today: Proceedings* 6, 333-339 (2019).

[3] Wang, Z.-H. & Jin, G. Silicon surface modification with a mixed silanes layer to immobilise proteins for biosensor with imaging ellipsometry. *Colloids and Surfaces B: Biointerfaces* 34, 173-177 (2004).

[4] Li, Y., Wang, J. & Cai, C. Rapid grafting of Azido-Labeled Oligo(ethylene glycol)s onto an Alkynyl-Terminated Monolayer on Nonoxidized Silicon via Microwave-Assisted "Click" Reaction, *Langmuir* 27, 2437-2445 (2011).

The invention claimed is:

1. A concentration sensor structure for at least one given species in a liquid medium, the concentration sensor structure comprising:
- a support;
- a waveguide;
- an optical resonator suspended from the support, said optical resonator being optically coupled to the waveguide; and
- a mechanical resonator suspended from the support, said mechanical resonator and said optical resonator being coupled, said mechanical resonator being configured to vibrate in volume mode and including a face extending in a plane of the concentration sensor structure and configured to receive molecules of said at least one given species, wherein
- said face includes a functionalization layer specific to said at least one given species, said face being a functionalization face,
- said mechanical resonator has a smaller dimension in a direction normal to the plane of the concentration sensor structure compared with dimensions of said face,
- the functionalization layer has a thickness less than or equal to 20 nm and includes functionalization molecules, a number of the molecules per surface unit of the functionalization face being uniform; and
- the functionalization layer is formed on a surface of the mechanical resonator, either in direct contact therewith or via a grafting layer configured to chemically attach the functionalization molecules of the functionalization layer, the grafting layer being formed in direct contact with the surface of the mechanical resonator or on a metallic bonding layer formed in direct contact with the surface of the mechanical resonator.

2. The concentration sensor structure according to claim 1, wherein the functionalization layer includes a number of grafting sites in each surface unit that varies by less than $5/100^{th}$ around an average, over all of the surface units of the functionalization face, of the number of the grafting sites in each of the surface units.

3. The concentration sensor structure according to claim 1, wherein a dimension of the mechanical resonator and/or of the optical resonator in the direction normal to the plane of the concentration sensor structure is at least 10 times smaller than dimensions of the mechanical resonator and/or of the optical resonator in the plane of the concentration sensor structure.

4. The concentration sensor structure according to claim 1, wherein the mechanical resonator is configured to vibrate in a radial mode.

5. The concentration sensor structure according to claim 1, wherein at least one of the mechanical resonator or the optical resonator is suspended by a foot connecting a face of the optical resonator facing the support and the support.

6. The concentration sensor structure according to claim 5, wherein the foot has a diameter at least 10 times smaller than in-plane dimensions of the optical resonator.

7. The concentration sensor structure according to claim 1, wherein the optical resonator and the mechanical resonator are a same element suspended from the support, said element being an optomechanical resonator.

8. The concentration sensor structure according to claim 7, wherein the optomechanical resonator has a shape of a disc, a ring, or a racecourse.

9. The concentration sensor structure according to claim 8, wherein the functionalization layer has a ring shape and borders a face of the optomechanical resonator.

10. The concentration sensor structure according to claim 1, further comprising a passivation layer at least on the support.

11. The concentration sensor structure according to claim 10, wherein the passivation layer is arranged on a face of the mechanical resonator inside a ring.

12. The concentration sensor structure according to claim 1, further comprising means for exciting the mechanical resonator so as to vibrate the mechanical resonator.

13. The concentration sensor structure according to claim 12, wherein the means for exciting the mechanical resonator vibrates the mechanical resonator at a resonant frequency.

14. The concentration sensor structure according to claim 1, further comprising a plurality of sets of coupled optical and mechanical resonators or a plurality of optomechanical resonators, coupled to the waveguide.

15. A concentration sensor for the at least one given species in the liquid medium, the concentration sensor comprising:
- the concentration sensor structure according to claim 1;
- a light source connected to one end of the waveguide; and
- means for processing a light wave connected to an other end of the waveguide.

16. The concentration sensor according to claim 15, wherein
- the light source is configured to emit multiplexed light waves, and
- the means for processing is configured to process the multiplexed light waves.

17. A measurement assembly, comprising:
- at least two of the concentration sensors according to claim 15, including
  - a first sensor, being functionalized with a first biological molecule specifically recognizing the at least one given species, and
  - a second sensor, being functionalized with a second biological molecule similar in nature to the first biological molecule and having a capacity for specific recognition of a species other than the at least one given species, said measurement assembly further including means for subtracting a signal emitted by the second sensor from a signal emitted by the first sensor.

18. A microfluidic system, comprising:
- at least one channel or a circulation of the liquid medium, a concentration of the at least one given species of which is to be measured; and
- the concentration sensor according to claim 15, or
- at least one assembly comprising:
  - at least two of the concentration sensors according to claim 15, including
    - a first sensor, being functionalized with a first biological molecule specifically recognizing the given at least one species, and
    - a second sensor, being functionalized with a second biological molecule similar in nature to the first biological molecule and having a capacity for specific recognition of a species other than the given at least one species, said assembly including means for subtracting a signal emitted by the second sensor from a signal emitted by the first sensor, the optical resonator and the mechanical resonator or an optomechanical resonator being disposed in the channel.

19. The microfluidic system according to claim 18, further comprising a channel with a plurality of sensors including functionalization layers specific to species different from each other.

20. The microfluidic system according to claim 18, wherein the channel has a height between 5 μm and 500 μm and a width between 10 μm and 700 μm.

* * * * *